US00PP19491P2

(12) United States Plant Patent
Michalik

(10) Patent No.: US PP19,491 P2
(45) Date of Patent: Nov. 25, 2008

(54) ***GERANIUM* PLANT NAMED 'SWEBERRY'**

(50) Latin Name: *Pelargonium×hortorum*
Varietal Denomination: Sweberry

(75) Inventor: Andrea Michalik, Fanny-Lewald Str. (DE)

(73) Assignee: Elsner PAC Jungpflanzen, Dresden (DE)

( * ) Notice: Subject to any disclaimer, the term of this patent is extended or adjusted under 35 U.S.C. 154(b) by 0 days.

(21) Appl. No.: 11/731,879

(22) Filed: Mar. 30, 2007

(51) Int. Cl.
*A01H 5/00* (2006.01)

(52) U.S. Cl. ..... Plt./328
(58) Field of Classification Search ..... Plt./328, Plt./325
See application file for complete search history.

(56) References Cited

PUBLICATIONS

UPOV–ROM GTITM, Plant Variety Database, 2007/04, GTI Jouve Retrieval Software, citation for 'Sweberry'.*

* cited by examiner

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of Zonal *Geranium* plant named 'Sweberry', characterized by its upright and rounded plant habit; freely branching habit; moderately vigorous growth habit; freely flowering habit; semi-double red purple-colored flowers with a red-colored blotch; and good garden performance.

1 Drawing Sheet

Botanical designation: *Pelargonium×hortorum.*
Cultivar denomination: 'Sweberry'.

BACKGROUND OF THE INVENTION

The present invention relates to a new and distinct cultivar of Zonal *Geranium*, botanically known as *Pelargonium×hortorum,* and hereinafter referred to by the name 'Sweberry'.

The new Zonal *Geranium* is a product of a planned breeding program conducted by the Inventor in Dresden, Germany. The objective of the breeding program is to create new Zonal *Geranium* cultivars with early flowering habit and attractive foliage and flower coloration.

The new Zonal *Geranium* originated from a cross-pollination made by the Inventor in Dresden, Germany during the summer of 2001 of two unnamed proprietary selections of *Pelargonium×hortorum,* not patented. The cultivar Sweberry was discovered and selected by the Inventor as a flowering plant from within the progeny of the stated cross-pollination in a controlled environment in Dresden, Germany in June, 2002.

Asexual reproduction of the new Zonal *Geranium* by vegetative terminal cuttings in a controlled environment in Dresden, Germany since January, 2003, has shown that the unique features of this new Zonal *Geranium* are stable and reproduced true to type in successive generations.

SUMMARY OF THE INVENTION

The cultivar Sweberry has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sweberry'. These characteristics in combination distinguish 'Sweberry' as a new and distinct cultivar of Zonal *Geranium:*

1. Upright and rounded plant habit.
2. Freely branching habit.
3. Moderately vigorous growth habit.
4. Freely flowering habit.
5. Semi-double red purple-colored flowers with a red-colored blotch.
6. Good garden performance.

Plants of the new Zonal *Geranium* differ primarily from plants of the parent selections in plant vigor and flower color.

Plants of the new Zonal *Geranium* can be compared to plants of the *Pelargonium×hortorum* cultivar Swevio, disclosed in U.S. Plant Pat. No. 17,386. In side-by-side comparisons conducted in Dresden, Germany, plants of the new Zonal *Geranium* differed from plants of the cultivar Swevio in the following characteristics:

1. Plants of the new Zonal *Geranium* were less compact and more vigorous than plants of the cultivar Swevio.
2. Leaves of plants of the new Zonal *Geranium* had a zonation pattern whereas leaves of plants of the cultivar Swevio did not have a zonation pattern.
3. Plants of the new Zonal *Geranium* had larger flower umbels with more flowers per umbel than plants of the cultivar Swevio.
4. Plants of the new Zonal *Geranium* had larger flowers than plants of the cultivar Swevio.
5. Plants of the new Zonal *Geranium* and the cultivar Swevio differed slightly in flower color.
6. Plants of the new Zonal *Geranium* had longer peduncles and pedicels than plants of the cultivar Swevio.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately describe the colors of the new Zonal *Geranium*. The photograph comprises a side perspective view of a typical flowering plant of 'Sweberry' grown in a container.

DETAILED BOTANICAL DESCRIPTION

The aforementioned photograph and following observations, measurements and values describe plants grown in Dresden, Germany in a glass-covered greenhouse during the summer and under conditions which closely approximate commercial *Geranium* production. During the production of the plants, day temperatures averaged 18° C., night temperatures averaged 16° C. and light levels ranged from 15 kilolux to 100 kilolux. Plants were about nine months old when the photograph and the description were taken. In the detailed description, color references are made to The Royal Horticultural Society Colour Chart, 1995 Edition, except where general terms of ordinary dictionary significance are used.

Botanical classification: *Pelargonium×hortorum* cultivar Sweberry.

Parentage:

*Female, or seed, parent.*—Unnamed proprietary selection of *Pelargonium×hortorum,* not patented.

*Male or pollen parent.*—Unnamed proprietary selection of *Pelargonium×hortorum,* not patented.

Propagation:

*Type.*—By vegetative terminal cuttings.

*Time to initiate roots, summer.*—About 18 days at temperatures of 22° C.

*Time to initiate roots, winter.*—About 22 days at temperatures of 22° C.

*Time to produce a rooted young plant, summer.*—About 25 days at temperatures of 22° C.

*Time to produce a rooted young plant, winter.*—About 30 days at temperatures of 22° C.

*Root description.*—Fine, fibrous; white in color.

*Rooting habit.*—Freely branching; dense.

Plant description:

*Plant/growth habit.*—Upright to rounded plant habit; densely foliated. Moderately vigorous growth habit. Freely basal branching habit with about twenty lateral branches developing per plant.

*Plant height, to top of umbels.*—About 40 cm.

*Plant height, to top of leaves.*—About 30 cm.

*Plant width.*—About 50 cm.

*Lateral branches.*—Length: About 15 cm. Diameter: About 8 mm. Internode length: About 1 cm to 2 cm. Texture: Pubescent. Color: 146B.

Foliage description:

*Arrangement.*—Alternate and opposite; simple.

*Length.*—About 6 cm.

*Width.*—About 10 cm.

*Shape.*—Reniform.

*Apex.*—Rounded.

*Base.*—Cordate.

*Margin.*—Bi-crenate.

*Venation pattern.*—Palmate.

*Texture, upper and lower surfaces.*—Pubescent.

*Color.*—Developing foliage, upper surface: 146A. Developing foliage, lower surface: 146B. Fully expanded foliage, upper surface: 137A; venation, 146A. Fully expanded foliage, lower surface: 137C; venation, 146D. Zonation pattern: Location of zone: About 1 cm from leaf margin. Width: About 3 cm. Color: 147A. Petiole: Length: About 8 cm to 11 cm. Diameter: About 3 mm. Texture, upper and lower surfaces: Rough. Color, upper and lower surfaces: 146B.

Flower description:

*Flower arrangement.*—Semi-double rotate flowers arranged in rounded hemispherical umbels arising from apical leaf axils. Umbels displayed above the foliage on strong peduncles. Flowers face upright to outward; flowers slightly cupped. Flowers persistent. Flowers not fragrant.

*Quantity of flowers.*—Freely flowering habit; about 22 to 26 flower buds and open flowers per umbel.

*Flowering season.*—Year-round under greenhouse conditions. In the garden in Dresden, Germany, flowering is continuous from April until frost in autumn.

*Flower longevity.*—Individual flowers last about six to ten days on the plant; umbels last about three to four weeks on the plant.

*Umbel height.*—About 6 cm.

*Umbel diameter.*—About 11 cm.

*Flower diameter.*—About 5 cm.

*Flower depth (height).*—About 2 cm.

*Flower buds.*—Length: About 1 cm. Diameter: About 6 mm. Shape: Elliptic. Color: 146C.

*Petals.*—Quantity per flower: About seven to nine. Length: About 2.4 cm. Width: About 2.7 cm. Shape: Fan-shaped. Apex: Rounded. Base: Attenuate. Margin: Entire. Texture, upper and lower surfaces: Smooth, glabrous; velvety. Color: When opening and fully opened, upper surface: Between 66A and 74A; blotch, 53A; towards the base, 56D; venation, similar to petal color. When opening and fully opened, lower surface: 66C; towards the base, 56D; venation, 66C.

*Sepals.*—Quantity per flower: Five, arranged in a single whorl. Length: About 1 cm to 1.2 cm. Width: About 3 mm to 4 mm. Shape: Lanceolate. Apex: Acute. Margin: Entire. Texture, upper and lower surfaces: Smooth. Color, upper and lower surfaces: 144A.

*Peduncle (umbel stem).*—Length: About 17 cm to 23 cm. Diameter: About 5 mm. Strength: Strong. Angle: Mostly erect. Texture: Pubescent. Color: 146C.

*Pedicel (individual flower stem).*—Length: About 3 cm. Diameter: About 2 mm. Strength: Moderately strong; flexible. Texture: Slightly pubescent. Color: 146C.

*Reproductive organs.*—Androecium: Stamen quantity per flower: About five to nine. Anther length: About 1 mm to 2 mm. Anther shape: Oblong. Anther color: Brown. Pollen amount: Scarce. Pollen color: Golden brown. Gynoecium: Pistil quantity per flower: One. Pistil length: About 8 mm to 10 mm. Stigma shape: Five-parted. Stigma color: Close to 74A. Style length: About 3 mm to 4 mm. Style color: Close to 74A. Ovary color: Close to 138D.

*Seed/fruit.*—Seed and fruit development have not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind and temperatures ranging from about 0° C. to about 35° C. and have demonstrated good garden performance.

It is claimed:

1. A new and distinct cultivar Zonal *Geranium* plant named 'Sweberry' as illustrated and described.

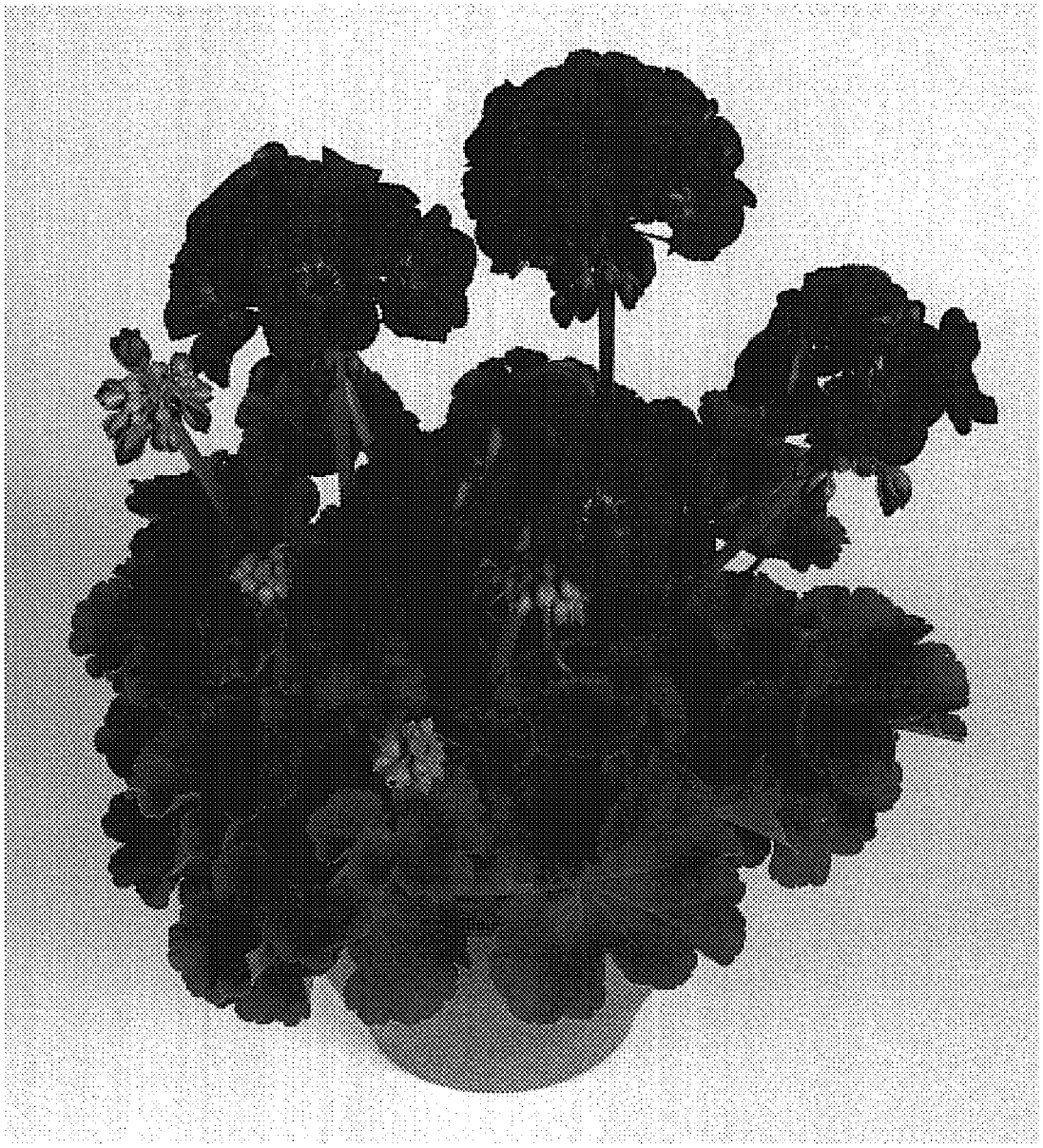

* * * * *